(12) United States Patent
Itoh et al.

(10) Patent No.: US 10,297,857 B2
(45) Date of Patent: May 21, 2019

(54) LITHIUM-ION BATTERY

(71) Applicant: HITACHI CHEMICAL COMPANY, LTD., Tokyo (JP)

(72) Inventors: Shingo Itoh, Tokyo (JP); Manabu Ochida, Tokyo (JP); Takanori Kajimoto, Tokyo (JP); Youhei Itoh, Tokyo (JP); Tadashi Yoshiura, Tokyo (JP)

(73) Assignee: HITACHI CHEMICAL COMPANY, LTD, Tokyo (JP)

(*) Notice: Subject to any disclaimer, the term of this patent is extended or adjusted under 35 U.S.C. 154(b) by 0 days.

(21) Appl. No.: 15/528,040

(22) PCT Filed: Nov. 18, 2015

(86) PCT No.: PCT/JP2015/082441
§ 371 (c)(1),
(2) Date: May 18, 2017

(87) PCT Pub. No.: WO2016/080457
PCT Pub. Date: May 26, 2016

(65) Prior Publication Data
US 2017/0331145 A1 Nov. 16, 2017

(30) Foreign Application Priority Data
Nov. 19, 2014 (JP) .................................. 2014-235087

(51) Int. Cl.
*H01M 10/0525* (2010.01)
*H01M 10/056* (2010.01)
(Continued)

(52) U.S. Cl.
CPC ...... *H01M 10/0525* (2013.01); *C01D 15/005* (2013.01); *C07C 69/003* (2013.01);
(Continued)

(58) Field of Classification Search
CPC .... H01M 4/133; H01M 4/525; H01M 10/056; H01M 10/0525
See application file for complete search history.

(56) References Cited

U.S. PATENT DOCUMENTS 6,387,561 B1 * 5/2002 Nemoto ................. H01M 2/361
429/51
2012/0015238 A1 1/2012 Minami et al.
(Continued)

FOREIGN PATENT DOCUMENTS

JP 2000-294294 A 10/2000
JP 2001-202993 A 7/2001
(Continued)

OTHER PUBLICATIONS

International Search Report for PCT/JP2015/082441 dated Feb. 16, 2016; English translation submitted herewith (5 pages).

*Primary Examiner* — Karie O'Neill Apicella
(74) *Attorney, Agent, or Firm* — Fitch, Even, Tabin & Flannery, L.L.P.

(57) ABSTRACT

A lithium-ion battery with high safety is provided. A lithium-ion battery 20 includes an electrode group 6, an electrolyte, and a battery container 5 that contains the electrode group 6 and the electrolyte. The electrode group 6 is formed by stacking a positive electrode and a negative electrode via a separator. The positive electrode contains a composite oxide of lithium, nickel, manganese, and cobalt as a main positive active material. The negative electrode contains amorphous carbon as a main negative active material. The lithium-ion battery 20 has a discharge capacity of 20 Ah or more. The ratio (the value of Y/X) of a volume Y occupied by the electrolyte to a volume X of a void space in the battery container 5 is 0.65 or more.

16 Claims, 2 Drawing Sheets

(51) Int. Cl.
  *H01M 4/133* (2010.01)
  *H01M 4/525* (2010.01)
  *C01D 15/00* (2006.01)
  *C07C 69/003* (2006.01)
  *H01M 2/36* (2006.01)
  *H01M 10/0587* (2010.01)
  *H01M 4/587* (2010.01)

(52) U.S. Cl.
  CPC ............ *H01M 2/361* (2013.01); *H01M 4/133* (2013.01); *H01M 4/525* (2013.01); *H01M 10/056* (2013.01); *H01M 10/0587* (2013.01); *H01M 4/587* (2013.01)

(56) References Cited

U.S. PATENT DOCUMENTS

| | | |
|---|---|---|
| 2015/0017499 A1 | 1/2015 | Nishiyama et al. |
| 2016/0006077 A1 | 1/2016 | Okumura et al. |

FOREIGN PATENT DOCUMENTS

| | | | | |
|---|---|---|---|---|
| JP | 2010-113804 A | | 5/2010 | |
| JP | 2010113804 A | * | 5/2010 | .......... H01M 10/058 |
| JP | 2012-038702 A | | 2/2012 | |
| JP | 2012-252807 A | | 12/2012 | |
| JP | 2012-256542 A | | 12/2012 | |
| JP | 2014-036010 A | | 2/2014 | |
| WO | 2013/128677 A1 | | 9/2013 | |
| WO | 2013/129182 A1 | | 9/2013 | |

* cited by examiner

LITHIUM-ION BATTERY

CROSS-REFERENCE TO RELATED APPLICATIONS

This application is a U.S. national phase application filed under 35 U.S.C. § 371 of International Application No. PCT/JP2015/082441, filed Nov. 18, 2015, designating the United States, which claims priority from Japanese Application No. 2014-235087 filed Nov. 19, 2014, which are hereby incorporated herein by reference in their entirety for all purposes.

TECHNICAL FIELD

The present invention relates to a lithium-ion battery.

BACKGROUND ART

Lithium-ion batteries are secondary batteries with a high energy density, and their characteristics are demonstrated when used as power sources for portable devices such as notebook computers and cellular phones. There are a variety of shapes of the lithium-ion batteries. Cylindrical lithium-ion batteries adopt a structure in which a positive electrode, a negative electrode, and a separator are wound. For example, two belt-like metal foils, to which a positive electrode material and a negative electrode material are applied, are stacked with a separator interposed therebetween to form a stacked member. Then, the stacked member is wound into a swirling shape to form a wound electrode group. The wound electrode group is contained in a cylindrical battery case that serves as a battery container, an electrolyte is poured into the battery case, and the battery case is sealed to form a cylindrical lithium-ion battery.

Among the cylindrical lithium-ion batteries, 18650-type lithium-ion batteries are widespread as lithium-ion batteries for consumer use. The 18650-type lithium-ion battery is small in outer dimension with a diameter of 18 mm and a height of about 65 mm. Lithium cobalt oxide with a high capacity and a long life is mainly used as the positive active material of the 18650-type lithium-ion battery. The 18650-type lithium-ion battery has a battery capacity of about 1.0 Ah to 2.0 Ah (3.7 Wh to 7.4 Wh).

In recent years, there have been expectations not only for consumer use of the lithium-ion batteries for portable devices etc., but also for development of use of the lithium-ion batteries for large-scale power storage systems that utilize natural energy such as solar and wind power generation. The large-scale power storage systems require a power storage amount in the order of several megawatt-hours per system.

For example, Patent Document 1 (WO 2013/128677 A1) discloses a cylindrical lithium-ion battery that includes a cylindrical battery container and a wound electrode group formed by winding a stacked member of a positive electrode, a separator, and a negative electrode. The battery has a discharge capacity of 30 Ah or more. A positive active material mixture that contains a composite oxide of lithium and manganese is used for the positive electrode. A negative active material mixture that contains amorphous carbon is used for the negative electrode.

RELATED-ART DOCUMENTS

Patent Documents

Patent Document 1: WO 2013/128677 A1
Patent Document 2: JP 2012-252807 A

SUMMARY OF INVENTION

Technical Problems

If the positive active material which contains the composite oxide of lithium and manganese is used, the battery capacity may be low, and the manganese may be eluted, during cycle charging, which leads to reduced capacity. For this reason, in Patent Document 2 (JP 2012-252807 A), a composite oxide of lithium, nickel, manganese, and cobalt (NMC) of a layered structure is used as the positive active material. Use of this active material is expected to improve the capacity and the life.

However, the composite oxide of lithium, nickel, manganese, and cobalt (NMC) of a layered structure discharges a large amount of oxygen when overcharged and generates a large amount of heat, thereby causing a safety issue.

The lithium-ion battery may be continuously charged with a large current or is continuously discharging a large current when: <1> the lithium-ion battery is overcharged because of a failure in charge control system, <2> the battery is crashed because of an unexpected impact, <3> the battery is pierced with a foreign object, and <4> the battery is in an abnormal state such as an external short-circuit. In such cases, the electrolyte and the positive active material in the positive electrode rapidly and continuously react with each other, thereby generating a gas to raise the internal pressure in the battery container.

In general, the cylindrical lithium-ion batteries have an internal pressure reduction mechanism such as a safety valve or a cleavage valve operable to discharge the gas to the outside of the container when a predetermined internal pressure is reached in order to prevent a rise in internal pressure in the battery container. When the rapid and continuous chemical reaction as mentioned above occurs, the battery container may be broken (specifically, for example, cracked, swelled, and ignited) even if the internal pressure reduction mechanism is provided. In particular, such a rise in internal pressure is mainly caused by a reaction of the electrolyte, and an abrupt rise in temperature is observed in such an event. A system configured to detect voltage abnormality is provided in addition to the normal charge control system, in order that the system can be immediately stopped when the battery is overcharged.

When the battery is overcharged, however, the temperature is abruptly raised, which causes thermal runaway of the battery unless heat due to the temperature rise is efficiently released to the outside of the battery. When the thermal runaway occurs, the reaction inside the battery may not be ceased even if the system configured to detect voltage abnormality operates to stop the current, and the battery container may be broken (specifically, for example, cracked, swelled, and ignited). In order to further improve the safety of the battery when overcharged, it is important to detect voltage abnormality before the temperature starts abruptly rising and to immediately interrupt the current. That is, it is important to allow the voltage to reach a voltage, at which voltage abnormality is detected, in a stage where the temperature rise is small (in a situation in which the temperature has hardly been raised or the temperature rise is gentle, for example).

The present invention has been made in view of the foregoing issues, and it is an object of the present invention to provide a lithium-ion battery with high safety.

The foregoing and other objects and novel features of the present invention will become apparent from the description herein and the accompanying drawings.

Solution to Problems

A lithium-ion battery, which the present invention aims at improving, includes an electrode group, an electrolyte, and a battery container that contains the electrode group and the electrolyte. The electrode group is formed by stacking a positive electrode and a negative electrode via a separator. The positive electrode contains a composite oxide of lithium, nickel, manganese, and cobalt as a main positive active material. The negative electrode contains amorphous carbon as a main negative active material. The lithium-ion battery has a discharge capacity of 20 Ah or more. In the lithium-ion battery according to the present invention, a ratio (a value of Y/X) of a volume Y occupied by the electrolyte to a volume X of a void space in the battery container, with the electrode group being placed in the battery container, is adjusted to 0.65 or more. By adjusting the volume ratio (the value of Y/X) of the volume of the electrolyte which occupies the void space and the volume of the void space in battery container, in which the electrode group is placed, to 0.65 or more, it is possible to improve the safety of the lithium-ion battery when overcharged. Particularly in the lithium-ion battery having a discharge capacity of 20 Ah or more, it is possible to efficiently discharge heat accumulated inside the lithium-ion battery to the outside of the battery. That is, the voltage is allowed to reach a set voltage at which voltage abnormality is detected in a stage in which the temperature rise is small, and then the current can be shut down. As a result, it is possible to prevent thermal runaway of the lithium-ion battery when overcharged, and to prevent damage to the battery container.

By adjusting the value of Y/X to 0.8 or more, which is larger than 0.65, it is possible to more efficiently discharge heat accumulated inside the lithium-ion battery to the outside of the battery. As a result, the voltage is allowed to reach a set voltage at which voltage abnormality is detected in a situation where the temperature rises gently, and then the current can be shut down, thereby reliably preventing thermal runaway of the lithium-ion battery. Further, if the value of Y/X is increased to 0.9 or more, which is larger than 0.8, the voltage is allowed to reach a set voltage at which voltage abnormality is detected in a situation where the temperature hardly rises, and then the current can be shut down, thereby more reliably preventing thermal runaway of the lithium-ion battery.

Effect of Invention

According to the present invention, it is possible to provide a lithium-ion battery with high safety.

DESCRIPTION OF EMBODIMENT

In the following description of the embodiment, the "range of A to B" indicates the range of A or more and B or less unless otherwise specified.

Embodiment

First, an overview of a lithium-ion secondary battery will be briefly described. The lithium-ion battery includes a positive electrode, a negative electrode, a separator, and an electrolyte in a battery container. The separator is disposed between the positive electrode and the negative electrode.

To charge the lithium-ion battery, an output terminal of a charger is connected between a positive terminal and a negative terminal. During charging, lithium ions inserted into the positive active material are desorbed and discharged into the electrolyte. The lithium ions discharged into the electrolyte move in the electrolyte, and pass through the separator which is formed from a microporous film to reach the negative electrode. The lithium ions having reached the negative electrode are inserted into the negative active material in the negative electrode.

To discharge a current from the lithium-ion battery, an external load is connected between the positive terminal and the negative terminal. During discharging, lithium ions inserted into the negative active material are desorbed and discharged into the electrolyte. In this event, electrons are discharged from the negative electrode. The lithium ions discharged into the electrolyte move in the electrolyte, and pass through the separator which is formed from a microporous film to reach the positive electrode. The lithium ions having reached the positive electrode are inserted into the positive active material in the positive electrode. In this event, electrons flow into the positive electrode when the lithium ions are inserted into the positive active material. In this way, discharging is done when the electrons move from the negative electrode to the positive electrode.

In this way, charging and discharging of the lithium-ion battery can be done when the lithium ions are inserted and desorbed between the positive active material and the negative active material. An example of the actual configuration of the lithium-ion battery will be discussed later (see FIG. 2, for example).

In the lithium-ion battery according to the embodiment, the ratio (the value of Y/X) of the volume Y occupied by the electrolyte to the volume X of a void space in the battery container, with the electrode group being placed in the battery container, is 0.65 or more. This improves the safety of the battery when overcharged. This effect is particularly remarkable for a lithium-ion battery with a discharge capacity of 20 Ah or more.

In the lithium-ion battery with a discharge capacity of 20 Ah or more, heat accumulated inside the lithium-ion battery is not easily discharged. Heat can be efficiently released to the outside when the ratio (the value of Y/X) of the volume Y occupied by the electrolyte to the volume X of a void space in the battery container, with the electrode group being placed in the battery container, is 0.65 or more. Therefore, it is presumed that the voltage is allowed to reach a set voltage at which voltage abnormality is detected in a stage where the temperature rise is small, and then the current can be shut down, thereby preventing thermal runaway from being caused and improving the safety. The set voltage at which voltage abnormality is detected is preferably 120 to 150%, more preferably 120 to 130%, with respect to the upper limit voltage when the battery is used.

The value of Y/X is 0.65 or more. From the viewpoint of more efficiently discharging heat to the outside of the battery, that is, in order that the voltage may reach a set voltage at which voltage abnormality is detected in a situation in which the temperature rise is gentle, the value of Y/X is preferably 0.8 or more. In order that the voltage may reach a set voltage at which voltage abnormality is detected in a situation in which the temperature has hardly been raised, the value of Y/X is preferably 0.9 or more.

The upper limit of the value of Y/X is not specifically limited. From the viewpoint of preventing leakage of the electrolyte, the value of Y/X is preferably less than 1, more preferably 0.98 or less, further more preferably 0.95 or less.

1. Positive Electrode

In the embodiment, the following positive electrode that is applicable to the lithium-ion battery is provided. The positive electrode (positive plate) according to the embodiment includes a current collector and a positive mixture formed thereon. The positive mixture is a layer provided on top of the current collector and including at least a positive active material.

A positive active material that mainly includes a layered composite oxide of lithium, nickel, manganese, and cobalt (hereinafter occasionally referred to as "NMC") is used. The NMC is a positive active material with a high capacity.

From the viewpoint of the safety, a mixed active material of the NMC and a spinel-type oxide of lithium and manganese (hereinafter occasionally referred to as "sp-Mn") may be used.

From the viewpoint of increasing the capacity of the battery, the content of the NMC is preferably 65% by mass or more, more preferably 70% by mass or more, further more preferably 80% by mass or more, with respect to the total amount of the positive mixture.

A composition represented by the following composition formula (Chemical Formula 1) is preferably used as the NMC.

$$Li_{(1+\delta)}Mn_xNi_yCo_{(1-x-y-z)}M_zO_2 \quad \text{(Chemical Formula 1)}$$

In the composition formula (Chemical Formula 1), $(1+\delta)$ indicates the composition ratio of Li (lithium), x indicates the composition ratio of Mn (manganese), y indicates the composition ratio of Ni (nickel), and $(1-x-y-z)$ indicates the composition ratio of Co (cobalt). z indicates the composition ratio of an element M. The composition ratio of O (oxygen) is 2.

The element M is at least one kind of element selected from the group consisting of Ti (titanium), Zr (zirconium), Nb (niobium), Mo (molybdenum), W (tungsten), Al (aluminum), Si (silicon), Ga (gallium), Ge (germanium), and Sn (tin).

Expressions $-0.15<\delta<0.15$, $0.1<x\leq0.5$, $0.6<x+y+z<1.0$, and $0\leq z\leq0.1$ are met.

A composition represented by the following composition formula (Chemical Formula 2) is preferably used as the sp-Mn.

$$Li_{(1+\eta)}Mn_{(2-\lambda)}M'_\lambda O_4 \quad \text{(Chemical Formula 2)}$$

In the composition formula (Chemical Formula 2), $(1+\eta)$ indicates the composition ratio of Li, $(2-\lambda)$ indicates the composition ratio of Mn, and $\lambda$ indicates the composition ratio of the element M'. The composition ratio of O (oxygen) is 4.

The element M' is preferably at least one kind of element selected from the group consisting of Mg (magnesium), Ca (calcium), Sr (strontium), Al, Ga, Zn (zinc), and Cu (copper).

Expressions $0\leq\eta\leq0.2$ and $0\leq\lambda\leq0.1$ are met.

Mg or Al is preferably used as the element M' in the composition formula (Chemical Formula 2). Use of Mg or Al can extend the life of the battery. The safety of the battery can also be improved. Further, addition of the element M' can reduce the elution of Mn, which can improve storage properties and charge/discharge cycle characteristics.

Materials other than the NMC and the sp-Mn may be used as the positive active material. Materials normally used in this field of the art can be used as the positive active material other than the NMC and the sp-Mn. Examples include lithium-containing composite metal oxides other than the NMC and the sp-Mn, olivine-type lithium salts, chalcogen compounds, and manganese dioxide.

The lithium-containing composite metal oxide is a metal oxide containing lithium and a transition metal or a metal oxide in which a part of the transition metal in the metal oxide has been replaced with a different type of element. Examples of the different type of element include Na, Mg, Sc, Y, Mn, Fe, Co, Ni, Cu, Zn, Al, Cr, Pb, Sb, V, and B. Mn, Al, Co, Ni, and Mg are preferable. One or two or more kinds of the different types of elements may be used.

Examples of the lithium-containing composite metal oxides other than the NMC and the sp-Mn include $Li_xCoO_2$, $Li_xNiO_2$, $Li_xMnO_2$, $Li_xCo_yNi_{1-y}O_2$, $Li_xCo_yM_{1-y}O_z$, and $Li_xNi_{1-y}M_yO_z$ (in the formulas, M indicates at least one kind of element selected from the group consisting of Na, Mg, Sc, Y, Mn, Fe, Co, Ni, Cu, Zn, Al, Cr, Pb, Sb, V, and B; x=0 to 1.2, y=0 to 0.9, and z=2.0 to 2.3). The value of x which indicates the molar ratio of lithium is increased and decreased by charging and discharging.

Examples of the olivine-type lithium salt include $LiFePO_4$. Examples of the chalcogen compound include titanium dioxide and molybdenum disulfide. The examples of the positive active material may be used singly or in a combination of two or more thereof.

Next, the positive mixture and the current collector will be described in detail below. The positive mixture contains a positive active material, a binding material, and so forth, and is formed on the current collector. The method of forming the positive mixture is not limited. For example, the positive mixture is formed as follows. The positive active material, the binding material, and other materials that are used as necessary such as a conductive material and a viscosity improver are dry-mixed into a sheet shape, and the mixture is pressure-bonded to the current collector (dry method). Alternatively, the positive active material, the binding material, and other materials that are used as necessary such as a conductive material and a viscosity improver are dissolved or dispersed in a dispersion solvent to prepare a slurry, and the slurry is applied to the current collector and dried (wet method).

A layered composite oxide of lithium, nickel, manganese, and cobalt (NMC) is used as the positive active material as discussed earlier. These materials are used in a powdery form (granular form), and mixed with each other.

Grains of the positive active material such as the NMC and the sp-Mn may be in a clumped shape, a polygonal shape, a spherical shape, an elliptical shape, a plate-like shape, a needle-like shape, a columnar shape, or the like.

The median size d50 of the grains of the positive active material such as the NMC and the sp-Mn (if primary grains are agglomerated to form secondary grains, the median size d50 of the secondary grains) can be adjusted in the following range. The lower limit of the range is 1 µm or more, preferably 3 µm or more, more preferably 5 µm or more. The upper limit of the range is 30 µm or less, preferably 25 µm or less, more preferably 15 µm or less.

If the median size d50 is less than the lower limit, the tap density (filling properties) is reduced, and a desired tap density may not be obtained. If the median size d50 is more than the upper limit, it takes time for lithium ions in the grains to be diffused, which may lower the battery performance. If the median size d50 is more than the upper limit, the mixing properties of the grains with other materials such as a binding material and a conductive material may be lowered during formation of the electrode. Hence, if the mixture is slurried and applied, the mixture may not be uniformly applied, and streaks or the like may be left. The median size d50 can be calculated from grain size distribution obtained using a laser diffraction and scattering method.

When the primary grains are agglomerated to form secondary grains, the average grain size (also referred to as "average particle size") of the primary grains is in the following range. The lower limit of the range is 0.01 µm or more, preferably 0.05 µm or more, further more preferably 0.08 µm or more, particularly preferably 0.1 µm or more. The upper limit of the range is 3 µm or less, preferably 2 µm or less, more preferably 1 µm or less, particularly preferably 0.6 µm or less. If the average grain size is more than the upper range, spherical secondary grains are not easily formed, and the battery performance such as the output characteristics may be lowered because of a reduction in tap density (filling properties) or a reduction in specific surface area. If the average grain size is less than the lower limit, the crystallinity is reduced, which may degrade the reversibility of charge and discharge.

The BET specific surface area of the grains of the positive active material such as the NMC and the sp-Mn is in the following range. The lower limit of the range is 0.2 $m^2/g$ or more, preferably 0.3 $m^2/g$ or more, further more preferably 0.4 $m^2/g$ or more. The upper limit of the range is 4.0 $m^2/g$ or less, preferably 2.5 $m^2/g$ or less, further more preferably 1.5 $m^2/g$ or less. If the BET specific surface area is less than the lower limit, the battery performance may be lowered. If the BET specific surface area is more than the upper limit, the tap density is not easily increased, and the mixing properties of the grains with other materials such as a binding material and a conductive material may be lowered. Hence, the applicability of the mixture after being slurried and applied may be degraded. The BET specific surface area is a specific surface area (area per gram) calculated using a BET method.

Examples of the conductive material for the positive electrode include metal materials such as copper and nickel; black lead (graphite) such as natural graphite and artificial graphite; carbon black such as acetylene black; and carbonaceous materials including amorphous carbon such as needle coke. These may be used singly or in a combination of two or more thereof.

The content (amount or proportion to be added) of the conductive material with respect to the mass of the positive mixture is in the following range. The lower limit of the range is 0.01% by mass or more, preferably 0.1% by mass or more, more preferably 1% by mass or more. The upper limit of the range is 50% by mass or less, preferably 30% by mass or less, more preferably 15% by mass or less. If the content is less than the lower limit, the conductivity may be insufficient. If the content is more than the upper limit, the battery capacity may be lowered.

The binding material for the positive active material is not specifically limited. If the positive mixture is formed using an application method, a material with a good solubility or dispersibility in a dispersion solvent is selected. Specific examples include: resin-based polymers such as polyethylene, polypropylene, polyethylene terephthalate, polymethyl methacrylate, polyimide, aromatic polyamide, cellulose, and nitrocellulose; rubber-like polymers such as SBR (styrene-butadiene rubber), NBR (acrylonitrile-butadiene rubber), fluororubber, isoprene rubber, butadiene rubber, and ethylene propylene rubber; thermoplastic elastomeric polymers such as styrene-butadiene-styrene block copolymers or hydrogen additives thereof, EPDMs (ethylene-propylene-diene ternary copolymers), styrene-ethylene-butadiene-ethylene copolymers, and styrene-isoprene-styrene block copolymers or hydrogen additives thereof; soft resin-based polymers such as syndiotactic-1,2-polybutadiene, polyvinyl acetate, ethylene-vinyl acetate copolymers, and propylene-α-olefin copolymers; fluorine-based polymers such as polyvinylidene fluoride (PVdF), polytetrafluoroethylene, fluorinated polyvinylidene fluoride, polytetrafluoroethylene-ethylene copolymers, and polytetrafluoroethylene-vinylidene fluoride copolymers; and polymer compositions having ion conductivity for alkali metal ions (in particular, lithium ions). These may be used singly or in a combination of two or more thereof. From the viewpoint of the stability of the positive electrode, the fluorine-based polymers such as polyvinylidene fluoride (PVdF) and polytetrafluoroethylene-vinylidene fluoride copolymers is preferably used.

The content (amount or proportion to be added) of the binding material with respect to the mass of the positive mixture is in the following range. The lower limit of the range is 0.1% by mass or more, preferably 1% by mass or more, further more preferably 3% by mass or more. The upper limit of the range is 80% by mass or less, preferably 60% by mass or less, further more preferably 40% by mass or less, particularly preferably 10% by mass or less. If the content of the binding material is too low, the positive active material cannot be sufficiently bound, and the mechanical strength of the positive electrode may be insufficient, which may degrade the battery performance such as the cycle characteristics. Conversely, if the content is too high, the battery capacity or the conductivity may be lowered.

The layers formed on the current collector using the wet method or the dry method are preferably consolidated using a hand press or a roller press in order to improve the filling density of the positive active material.

The density of the positive mixture consolidated as described above is preferably 2.4 to 2.8 $g/cm^3$. From the viewpoint of further improving the input/output characteristics and the safety, the density is preferably 2.50 $g/cm^3$ or more and 2.75 $g/cm^3$ or less, more preferably 2.55 $g/cm^3$ or more and 2.70 $g/cm^3$ or less.

The amount of the positive mixture applied to one surface of the positive current collector is preferably 80 to 200 $g/m^2$. From the viewpoint of further improving the energy density and the input/output characteristics, the amount is preferably 110 $g/m^2$ or more and 160 $g/m^2$ or less, more preferably 120 $g/m^2$ or more and 150 $g/m^2$ or less.

In consideration of the amount of the positive mixture applied to one surface of the positive current collector and the density of the positive mixture described above, the thickness of the film of the positive mixture applied to one surface of the positive current collector ([thickness of positive electrode—thickness of positive current collector]/2) is preferably 39 to 68 µm, more preferably 43 to 64 µm, further more preferably 46 to 60 µm.

As described above, by determining the density of the positive mixture and the amount of the positive mixture to be applied to one surface of the positive current collector in the above ranges, it is possible to provide a high-capacity lithium-ion battery having a discharge capacity of 20 Ah or more and less than 99 Ah with high input/output and a high energy density while securing the safety.

The material of the current collector for the positive electrode is not specifically limited. Examples include metal materials such as aluminum, stainless steel, nickel plating, titanium, and tantalum; and carbonaceous materials such as a carbon cloth and carbon paper. Among these, the metal materials, particularly aluminum, are preferable.

The shape of the current collector is not specifically limited, and the materials may be processed into a variety of shapes. The metal materials may be a metal foil, a circular metal column, a metal coil, a metal plate, a thin metal film, expanded metal, punching metal, and foamed metal. The carbonaceous materials may be a carbon plate, a thin carbon film, and a circular carbon column. Among these, a thin metal film is preferably used. The thin film may be formed in a mesh shape as appropriate. The thickness of the thin film may be determined as desired, and may be in the following range. The lower limit of the range is 1 µm or more, preferably 3 µm or more, more preferably 5 µm or more. The upper limit of the range is 1 mm or less, preferably 100 µm or less, more preferably 50 µm or less. If the thickness is less than the lower limit, the sufficient strength required for the current collector may not be obtained. If the thickness is more than the upper limit, the flexibility of the thin film may be lowered to degrade the processability.

2. Negative Electrode

In the embodiment, the following negative electrode that is applicable to the lithium-ion secondary battery is provided. The negative electrode (negative plate) according to the embodiment includes a current collector and a negative mixture formed on both sides thereof. The negative mixture contains a negative active material capable of electrochemically occluding and releasing lithium ions.

The negative active material used in the embodiment is mainly amorphous carbon. The negative active material may also include carbon materials other than the amorphous carbon. The carbon materials are roughly divided into graphite-based carbon materials with a uniform crystalline structure and non-graphite-based carbon materials with a non-uniform crystalline structure. Examples of the graphite-based carbon materials include natural graphite and artificial graphite. Examples of the non-graphite-based carbon materials include amorphous carbon, which includes easily graphitizable carbon which is easily graphitizable by heating at 2000 to 3000° C. in spite of having a non-uniform crystalline structure, and non-easily graphitizable carbon which is not easily graphitizable. The amorphous carbon can be manufactured by performing a heat treatment on petroleum pitch, polyacene, polyparaphenylene, polyfurfuryl alcohol, and polysiloxane, for example, which can be formed into the non-easily graphitizable carbon or the easily graphitizable carbon by varying the sintering temperature. For example, sintering temperatures of about 500° C. to 800° C. are suitable to manufacture the non-easily graphitizable carbon, and sintering temperatures of about 800° C. to 1000° C. are suitable to manufacture the easily graphitizable carbon. The non-easily graphitizable carbon is defined as having a d002 value of 0.36 nm or more and 0.40 nm or less, the d002 value indicating the surface spacing in the C-axis direction obtained by a wide-angle X-ray diffraction method.

The easily graphitizable carbon preferably has a d002 value of 0.34 nm or more and 0.36 nm or less, the d002 value indicating the surface spacing in the C-axis direction obtained by a wide-angle X-ray diffraction method. The d002 value is more preferably 0.341 nm or more and 0.355 nm or less, further more preferably 0.342 nm or more and 0.35 nm or less.

The proportion of the content of the amorphous carbon is preferably 55% by mass or more, more preferably 70% by mass or more, further more preferably 90% by mass or more, with respect to the total amount of the negative active material. From the viewpoint of the battery characteristics, the easily graphitizable carbon is preferably used as the amorphous carbon. The easily graphitizable carbon and the non-easily graphitizable carbon may be used in combination with each other as the amorphous carbon.

The average grain size (median side d50) of the amorphous carbon is preferably 2 to 50 µm. If the average grain size is 2 µm or more, the specific surface area can be in an adequate range, the lithium-ion battery has high initial charge/discharge efficiency, and the grains contact each other well to provide good input/output characteristics. If the average grain size is 50 µm or less, short-circuit of the battery can be suppressed since asperities are not easily formed on the electrode surface, and the input/output characteristics of the lithium-ion battery tends to be improved since the diffusion distance of Li from the surface to the inside of the grains is relatively short. From this viewpoint, the average grain size is more preferably 5 to 30 µm, further more preferably 10 to 20 µm. The grain side distribution can be measured using a laser-diffraction grain size distribution measuring device (e.g. SALD-3000J manufactured by Shimadzu Corporation) by dispersing a sample in purified water containing a surfactant, for example, and the average grain size is calculated as 50% D.

Metal oxides such as tin oxide and silicon oxide, composite metal oxides, lithium alone, lithium alloys such as a lithium aluminum alloy, and materials that can form an alloy with lithium such as Sn and Si can be used in combination with each other as the negative active material. These may be used singly or in a combination of two or more thereof.

The composite metal oxide is not specifically limited as long as it can occlude and release lithium. From the viewpoint of the high-current-density charge/discharge characteristics, the composite metal oxide preferably contains Ti (titanium), Li (lithium), or both Ti and Li.

From the viewpoint of the input characteristics and a practical point of view, the SOC (State Of Charge) at a potential of 0.1 V relative to the lithium potential of the negative electrode according to the embodiment is preferably 65% or more and 90% or less, more preferably 68' or more and 85% or less. The SOC at a potential of 0.1 V relative to the lithium potential can be measured as follows, for example. First, a negative electrode formed by applying a negative mixture to one surface of a current collector is punched to have a diameter of 15 mm, and a CR2032 coin cell is fabricated in an atmosphere of argon from the negative electrode, lithium metal punched to have a diameter of 16 mm, a separator (e.g. a porous sheet made of polyethylene) punched to have a diameter of 19 mm, and an electrolyte (e.g. a carbonate-based electrolyte). The coil cell is charged to 0 V (V vs Li/Li$^+$) at a constant current with a current density of 0.1 C at 25° C., and charged at a constant voltage of 0 V until the current density becomes 0.01 C.

Next, a constant current with a current density of 0.1 C is discharged from the coin cell to 1.5 V (V vs Li/Li$^+$), and three cycles of such charge and discharge are performed. The charge capacity in the third cycle is determined as an SOC of 100%; the charge capacity at the time when 0.1 V is reached in the third cycle is measured; and the SOC is calculated from the following formula (1).

SOC=CC charge capacity to 0.1 V in third cycle/
    CCCV charge capacity to 0 V in third cycle    (Formula 1)

The material of the current collector for the negative electrode is not specifically limited. Examples include metal materials such as copper, nickel, stainless steel, and nickel-plated steel. Among these, copper is preferable from the viewpoint of the processability and the cost.

The shape of the current collector is not specifically limited, and the materials may be processed into a variety of shapes. Examples include a metal foil, a circular metal column, a metal coil, a metal plate, a thin metal film, expanded metal, punching metal, and foamed metal. Among these, a thin metal film is preferably used. A copper foil is more preferable. The copper foil includes a rolled copper foil formed by a rolling method and an electrolytic copper foil formed by an electrolytic method. Both the two types are suitable for use as the current collector.

The thickness of the current collector is not limited. If the thickness is less than 25 μm, the strength of the current collector can be improved by using a strong copper alloy (such as phosphor bronze, titanium copper, a corson alloy, and a Cu—Cr—Zr alloy), rather than pure copper.

From the viewpoint of the energy density and the input/output characteristics, the amount of the negative mixture applied to one surface of the current collector is preferably 50 g/m$^2$ or more and 120 g/m$^2$ or less, more preferably 60 g/m$^2$ or more and 100 g/m$^2$ or less.

The configuration of the negative mixture formed using the negative active material is not specifically limited. The negative mixture density is in the following range. The lower limit of the negative mixture density is preferably 0.7 g/cm$^3$ or more, more preferably 0.8 g/cm$^3$ or more, further preferably 0.9 g/cm$^3$ or more. The upper limit of the negative mixture density is 2 g/cm$^3$ or less, preferably 1.9 g/cm$^3$ or less, more preferably 1.8 g/cm$^3$ or less, further preferably 1.7 g/cm$^3$ or less.

If the negative mixture density is more than the upper limit, the grains of the negative active material are easily broken, which may increase the initial irreversible capacity or degrade the high-current-density charge/discharge characteristics because of a reduction in permeability of a non-aqueous electrolyte in the vicinity of the interface between the current collector and the negative active material. If the negative mixture density is less than the lower limit, the battery resistance is increased because of a reduction in conductivity in the negative active material, which may reduce the capacity per unit volume.

The binding material for the negative active material is not specifically limited as long as it is stable with respect to the non-aqueous electrolyte or the dispersion solvent used to form the electrode. Examples include: resin-based polymers such as polyethylene, polypropylene, polyethylene terephthalate, polymethyl methacrylate, aromatic polyamide, cellulose, and nitrocellulose; rubber-like polymers such as SBR (styrene-butadiene rubber), isoprene rubber, butadiene rubber, fluororubber, NBR (acrylonitrile-butadiene rubber), and ethylene propylene rubber; styrene-butadiene-styrene block copolymers or hydrogen additives thereof; thermoplastic elastomeric polymers such as EPDMs (ethylene-propylene-diene ternary copolymers), styrene-ethylene-butadiene-styrene copolymers, and styrene-isoprene-styrene block copolymers or hydrogen additives thereof; soft resin-based polymers such as syndiotactic-1,2-polybutadiene, polyvinyl acetate, ethylene-vinyl acetate copolymers, and propylene-α-olefin copolymers; fluorine-based polymers such as polyvinylidene fluoride, polytetrafluoroethylene, fluorinated polyvinylidene fluoride, and polytetrafluoroethylene-ethylene copolymers; and polymer compositions having ion conductivity for alkali metal ions (in particular, lithium ions). These may be used singly or in a combination of two or more thereof.

The dispersion solvent for forming the slurry is not limited to any type as long as the solvent is capable of dissolution or dispersion of the negative active material, the binding material, the conductive material and the viscosity improver which are used as necessary, and so forth. Either of an aqueous solvent and an organic solvent may be used. Examples of the aqueous solvent include water and a mixed solvent of alcohol and water. Examples of the organic solvent include N-methylpyrrolidone (NMP), dimethylformamide, dimethylacetamide, methyl ethyl ketone, cyclohexanone, methyl acetate, methyl acrylate, diethyltriamine, N,N-dimethylaminopropylamine, tetrahydrofuran (THF), toluene, acetone, diethyl ether, dimethylacetamide, hexamethylphosphoramide, dimethyl sulfoxide, benzene, xylene, quinoline, pyridine, methylnaphthalene, and hexane. If the aqueous solved is used, the viscosity improver is particularly preferably used. A dispersant etc. is added in addition to the viscosity improver, and the materials are slurried using latex such as SBR. The examples of the dispersion solvent may be used singly or in a combination of two or more thereof.

The content (amount or proportion to be added) of the binding material with respect to the mass of the negative mixture is in the following range. The lower limit of the range is preferably 0.1% by mass or more, more preferably 0.5% by mass or more, further more preferably 0.6% by mass or more. The upper limit of the range is 20% by mass or less, preferably 15% by mass or less, more preferably 10% by mass or less, further more preferably 8% by mass or less.

If the content is more than the upper limit, the proportion of the binding material which does not contribute to the battery capacity is increased, which may lower the battery capacity. If the content is less than the lower limit, the strength of the negative mixture may be lowered.

If the rubber-like polymer represented by SBR is used as the main component of the binding material, the content of the binding material with respect to the mass of the negative mixture is in the following range. The lower limit of the range is 0.1% by mass or more, preferably 0.5% by mass or more, more preferably 0.6% by mass or more. The upper limit of the range is 5% by mass or less, preferably 3% by mass or less, more preferably 2% by mass or less.

If the fluorine-based polymer represented by polyvinylidene fluoride is used as the main component of the binding material, the content of the binding material with respect to the mass of the negative mixture is in the following range. The lower limit of the range is 1% by mass or more, preferably 2% by mass or more, more preferably 3% by mass or more. The upper limit of the range is 15% by mass or less, preferably 10% by mass or less, more preferably 8% by mass or less.

The viscosity improver is used to adjust the viscosity of the slurry. The viscosity improver is not specifically limited. Examples of the viscosity improver include carboxymethyl cellulose, methyl cellulose, hydroxymethyl cellulose, ethyl cellulose, polyvinyl alcohol, oxidized starch, phosphorylated starch, casein, and salts thereof. These may be used singly or in a combination of two or more thereof.

If the viscosity improver is used, the content of the viscosity improver with respect to the mass of the negative mixture is in the following range. The lower limit of the range is 0.1% by mass or more, preferably 0.5% by mass or more, more preferably 0.6% by mass or more. The upper limit of the range is 5% by mass or less, preferably 3% by mass or less, more preferably 2% by mass or less.

If the content is less than the lower limit, the applicability of the slurry may be lowered. If the content is more than the upper limit, the proportion of the negative active material to the negative mixture is lowered, which may lower the battery capacity or increase the resistance among the negative active material.

3. Electrolyte

The electrolyte according to the embodiment is formed from a lithium salt (electrolyte) and a non-aqueous solvent for dissolution of the lithium salt. An additive may be added as necessary.

The lithium salt is not specifically limited as long as it is usable as the electrolyte of the non-aqueous electrolyte for the lithium-ion battery. Examples of the lithium salt include the following inorganic lithium salts, fluorine-containing organic lithium salts, and oxalateborate salts.

Examples of the inorganic lithium salt include inorganic fluoride salts such as $LiPF_6$, $LiBF_4$, $LiAsF_6$, and $LiSbF_6$, perhalogenated acid salts such as $LiClO_4$, $LiBrO_4$, and $LiIO_4$, and inorganic chloride salts such as $LiAlCl_4$.

Examples of the fluorine-containing organic lithium salt include perfluoroalkanesulfonic acid salts such as $LiCF_3SO_3$; perfluoroalkanesulfonylimide salts such as $LiN(CF_3SO_2)_2$, $LiN(CF_3CF_2SO_2)_2$, and $LiN(CF_3SO_2)(C_4F_9SO_2)$; perfluoroalkanesulfonylmethide salts such as $LiC(CF_3SO_2)_3$; and fluoroalkyl fluorophosphate salts such as $Li[PF_5(CF_2CF_2CF_3)]$, $Li[PF_4(CF_2CF_2CF_3)_2]$, $Li[PF_3(CF_2CF_2CF_3)_3]$, $Li[PF_5(CF_2CF_2CF_2CF_3)]$, $Li[PF_4(CF_2CF_2CF_2CF_3)_2]$, and $Li[PF_3(CF_2CF_2CF_2CF_3)_3]$.

Examples of the oxalateborate salt include lithium bis(oxalato)borate and lithium difluorooxalatoborate.

These lithium salts may be used singly or in a combination of two or more thereof. Among these, lithium hexafluorophosphate ($LiPF_6$) is preferable when comprehensively judging the solubility in the solvent, the charge/discharge characteristics when assembled in a secondary battery, the output characteristics, the cycle characteristics, and so forth.

The concentration of the electrolyte in the non-aqueous electrolyte is not specifically limited. The concentration of the electrolyte is in the following range. The lower limit of the concentration is 0.5 mol/L or more, preferably 0.6 mol/L or more, more preferably 0.7 mol/L or more. The upper limit of the concentration is 2 mol/L or less, preferably 1.8 mol/L or less, more preferably 1.7 mol/L or less. If the concentration is too low, the electrical conductivity of the electrolyte may be insufficient. If the concentration is too high, the viscosity is increased, which may lower the electrical conductivity. Such a reduction in electrical conductivity may lower the performance of the lithium-ion battery.

The non-aqueous solvent is not specifically limited as long as it is usable as the solvent for the electrolyte for the lithium-ion secondary battery. Examples include the following cyclic carbonates, chain carbonates, chain esters, cyclic ethers, and chain ethers.

Cyclic carbonates with an alkylene group having a carbon number of 2 to 6 are preferable, and cyclic carbonates with an alkylene group having a carbon number of 2 to 4 are more preferable. Examples include ethylene carbonate, propylene carbonate, and butylene carbonate. Among these, ethylene carbonate and propylene carbonate are preferable.

The chain carbonate is preferably dialkyl carbonate. Dialkyl carbonate with two alkyl groups having a carbon number of 1 to 5 is preferable, and dialkyl carbonate with two alkyl groups having a carbon number of 1 to 4 is more preferable. Examples include symmetric chain carbonates such as dimethyl carbonate, diethyl carbonate, and di-n-propyl carbonate; and asymmetric chain carbonates such as ethylmethyl carbonate, methyl-n-propyl carbonate, and ethyl-n-propyl carbonate. Among these, dimethyl carbonate, diethyl carbonate, and ethylmethyl carbonate are preferable.

Examples of the chain ester include methyl acetate, ethyl acetate, propyl acetate, and methyl propionate. Among these, use of methyl acetate is preferable from the viewpoint of improving the low-temperature characteristics.

Examples of the cyclic ether include tetrahydrofuran, 2-methyltetrahydrofuran, and tetrahydropyran. Among these, use of tetrahydrofuran is preferable from the viewpoint of improving the input/output characteristics.

Examples of the chain ether include dimethoxyethane and dimethoxymethane.

These may be used singly or in a combination of two or more thereof. A mixed solvent of two or more kinds of compounds is preferably used. A high-permittivity solvent such as cyclic carbonates and a low-viscosity solvent such as chain carbonates and chain esters are preferably used jointly. One of preferable combinations is a combination mainly including a cyclic carbonate and a chain carbonate. The proportion of the total of the cyclic carbonate and the chain carbonate to the non-aqueous solvent is 80% by volume or more, preferably 85% by volume or more, more preferably 90% by volume or more. Moreover, the volume of the cyclic carbonate to the total of the cyclic carbonate and the chain carbonate is preferably in the following range. The lower limit of the cyclic carbonate is 5% by volume or more, preferably 10% by volume or more, more preferably 15% by volume or more. The upper limit of the range is 50% by volume or less, preferably 35% by volume or less, more preferably 30% by volume or less. Such combinations of the non-aqueous solvent improves the cycle characteristics of the battery and the high-temperature storage characteristics (in particular, the remaining capacity after storage at a high temperature and the high-load discharge capacity).

The additive is not specifically limited as long as it is intended to be used for the non-aqueous electrolyte for the lithium-ion battery. Examples of the additive include heterocyclic compounds containing nitrogen, sulfur, or nitrogen and sulfur, cyclic carboxylate esters, fluorine-containing cyclic carbonates, and other compounds having an unsaturated bond in a molecule. From the viewpoint of extending the life of the battery, the fluorine-containing cyclic carbonates and the other compounds having an unsaturated bond in a molecule are preferable.

Examples of the fluorine-containing cyclic carbonate include fluoroethylene carbonate, difluoroethylene carbonate, trifluoroethylene carbonate, tetrafluoroethylene carbonate, and trifluoropropylene carbonate.

Examples of the other compounds having an unsaturated bond in a molecule include vinylene carbonate.

Besides the above additives, other additives such as an overcharge preventing material, a negative electrode coating forming material, a positive electrode protecting material, and a high-input/output material may be used according to the desired functions.

The above other additives can suppress an abrupt electrode reaction in case of abnormality due to overcharge, improve the capacity maintenance characteristics and the cycle characteristics after storage at a high temperature, and improve the input/output characteristics.

4. Separator

The separator is not specifically limited as long as it has ion permeability while electronically insulating the positive electrode and the negative electrode from each other and is resistant to the oxidizing on the positive electrode side and to the reducing on the negative electrode side. Resins, inorganic substances, glass fibers, and so forth are used as the material of the separator that meets such characteristics.

Examples of the resin include an olefin-based polymer, a fluorine-based polymer, a cellulose-based polymer, polyimide, and nylon. The resin is preferably selected from materials that are stable with respect to the non-aqueous electrolyte and have good liquid retention properties. Use of a porous sheet, a non-woven fabric, or the like made of a polyolefin such as polyethylene and polypropylene as the raw material is preferable.

Examples of the inorganic substance include oxides such as alumina and silicon dioxide, nitrides such as aluminum nitride and silicon nitride, and sulfates such as barium sulfate and calcium sulfate. The above inorganic substance in a fiber form or a grain form may be affixed to a base material in a thin film such as a non-woven fabric, a woven fabric, and a microporous film and may be used as the separator. The base material in a thin film preferably has a pore diameter of 0.01 to 1 μm and a thickness of 5 to 50 μm. The above inorganic substance in a fiber form or a grain form may be formed into a composite porous layer using a binding material such as a resin, for example, and may be used as the separator. Further, the composite porous layer may be formed on the surface of the positive electrode or the negative electrode and may be used as the separator. For example, a composite porous layer, which is formed by binding alumina grains having a 90% grain size of less than 1 μm using a fluorine resin as the binding material, may be formed on the surface of the positive electrode.

5. Other Constituent Members

A cleavage valve may be provided as other constituent members of the lithium-ion battery. When the cleavage valve is opened, a rise in pressure inside the battery can be suppressed, thereby increasing the safety of the battery.

A portion operable to discharges an inert gas (such as carbon dioxide, for example) to be generated with an increase in temperature may be provided. By providing such a portion, the cleavage valve can be more quickly opened by generation of the inert gas when the temperature inside the battery is raised, thereby improving the safety. Examples of the material used for such portion include lithium carbonate and a polyalkylene carbonate resin. Examples of the polyalkylene carbonate resin include polyethylene carbonate, polypropylene carbonate, poly(1,2-dimethylethylene carbonate), polybutene carbonate, polyisobutene carbonate, polypentene carbonate, polyhexene carbonate, polycyclopentene carbonate, polycyclohexene carbonate, polycycloheptene carbonate, polycyclooctene carbonate, and polylimonene carbonate. The material used for the component is preferably lithium carbonate, polyethylene carbonate, and polypropylene carbonate.

(Discharge Capacity of Lithium Ion Secondary Battery)

The lithium-ion battery according to the embodiment formed from the constituent elements described above has a discharge capacity of 20 Ah or more. From the viewpoint of attaining high input/output and a high energy density while securing the safety, the lithium-ion battery preferably has a discharge capacity of 30 Ah or more and less than 99 Ah, more preferably 40 Ah or more and less than 95 Ah.

(Capacity Ratio Between Negative Electrode and Positive Electrode of Lithium-Ion Battery)

In the embodiment, the capacity ratio between the negative electrode and the positive electrode (negative electrode capacity/positive electrode capacity) is preferably 1 or more and less than 1.40, more preferably 1.05 to 1.35, further more preferably 1.1 to 1.30, from the viewpoint of the safety and the energy density. If the capacity ratio is 1.40 or more, the positive electrode potential may be more than 4.2 V during charging and therefore the safety may be reduced (here, the positive electrode potential is a potential relative to Li).

The negative electrode capacity indicates the [discharge capacity of negative electrode]. The positive electrode capacity indicates the [initial charge capacity of positive electrode—larger one of irreversible capacities of negative electrode and positive electrode]. The [discharge capacity of negative electrode] is defined as being calculated by a charge/discharge device when lithium ions having been inserted into the negative active material are desorbed. The [initial charge capacity of positive electrode] is defined as being calculated by a charge/discharge device when lithium ions are desorbed from the positive active material.

The capacity ratio between the negative electrode and the positive electrode can also be calculated from "discharge capacity of lithium-ion battery/discharge capacity of negative electrode", for example. The discharge capacity of the lithium-ion battery can be measured by performing constant-current constant-voltage (CCCV) charge at 4.2 V and 0.1 to 0.5 C for 2 to 5 hours to the end, and thereafter performing constant-current (CC) discharge to 2.7 V at 0.1 to 0.5 C. The discharge capacity of the negative electrode of the embodiment can be calculated as follows: the negative electrode of a lithium-ion battery according to the embodiment, of which discharge capacity is to be measured, is cut into a predetermined area, fabricating a single-electrode cell using lithium metal as a counter electrode via a separator impregnated with an electrolyte; the discharge capacity per predetermined area is measured when the cell is subjected to constant-current (CC) discharge to 1.5V at 0.1 C after the cell is subjected to constant-current constant-voltage (CCCV) charge at 0 V and 0.1 C with an ending current of 0.01 C; and the measured discharge capacity is then converted into a value in terms of the total area of the negative electrode used in the lithium-ion battery according to the embodiment. In the single-electrode cell, the direction in which lithium ions are inserted into the negative active material is defined as "charge", and the direction in which the lithium ions having been inserted into the negative active material are desorbed is defined as "discharge".

C means "current value (A)/discharge capacity (Ah) of battery".

EXAMPLES

The embodiment will be described in further detail below based on examples. The present invention is not limited to the following examples.

[Fabrication of Positive Electrode]

The positive electrode was fabricated as follows. A layered composite oxide of lithium, nickel, manganese, and cobalt ($LiMn_{1/3}Ni_{1/3}Co_{1/3}O_2$) was used as the positive active material. Acetylene black as the conductive material and polyvinylidene fluoride as the binding material were sequentially added to the positive active material, and mixed to obtain a mixture of the positive electrode materials. The weight ratio was active material:conductive material:binding material=90:5:5. N-methyl-2-pyrrolidone (NMP) was further added as the dispersion solvent to the mixture, and kneaded to form a slurry. A predetermined amount of the slurry was substantially uniformly and equally applied to both surfaces of an aluminum foil with a thickness of 20 μm that works as the current collector for the positive electrode. The aluminum foil had a rectangular shape with a short side (width) of 570 mm, and had an unapplied portion, to which the slurry had not been applied, with a width of 85 mm along the long side on both sides. The foil was subjected to a drying process. The foil was bisected in the width direction to obtain two sheets. Then, the unapplied portion was cut, and the remaining uncut portions were used as lead pieces. The width of the lead pieces was 10 mm, and the interval between adjacent lead pieces was 20 mm. After that, the foil was consolidated to a predetermined density by pressing. The foil was cut again to obtain a positive electrode with a width of 195 mm.

[Fabrication of Negative Electrode]

The negative electrode was fabricated as follows. Easily graphitizable carbon was used as the negative active material. Polyvinylidene fluoride was added as the binding material to the easily graphitizable carbon. The weight ratio was active material:binding material=92:8. N-methyl-2-pyrrolidone (NMP) was added as the dispersion solvent to the mixture, and kneaded to form a slurry. A predetermined amount of the slurry was substantially uniformly and equally applied to both surfaces of a rolled copper foil with a thickness of 10 μm as the current collector for the negative electrode. The amount of the negative mixture applied was determined such that the capacity ratio between the negative electrode and the positive electrode (negative electrode capacity/positive electrode capacity) was 1.2. The rolled copper foil had a rectangular shape with a short side (width) of 570 mm, and had an unapplied portion, to which the slurry had not been applied, with a width of 80 mm along the long side on both sides. The foil was subjected to a drying process. The foil was bisected in the width direction to obtain two sheets. Then, the unapplied portion was cut, and the remaining uncut portions were used as lead pieces. The width of the lead pieces was 10 mm, and the interval between adjacent lead pieces was 20 mm. After that, the foil was consolidated to a predetermined density by pressing. The density of the negative mixture was 1.15 g/cm$^3$. The foil was cut again to obtain a negative electrode with a width of 196 mm.

[Fabrication of Battery]

Figure 2:
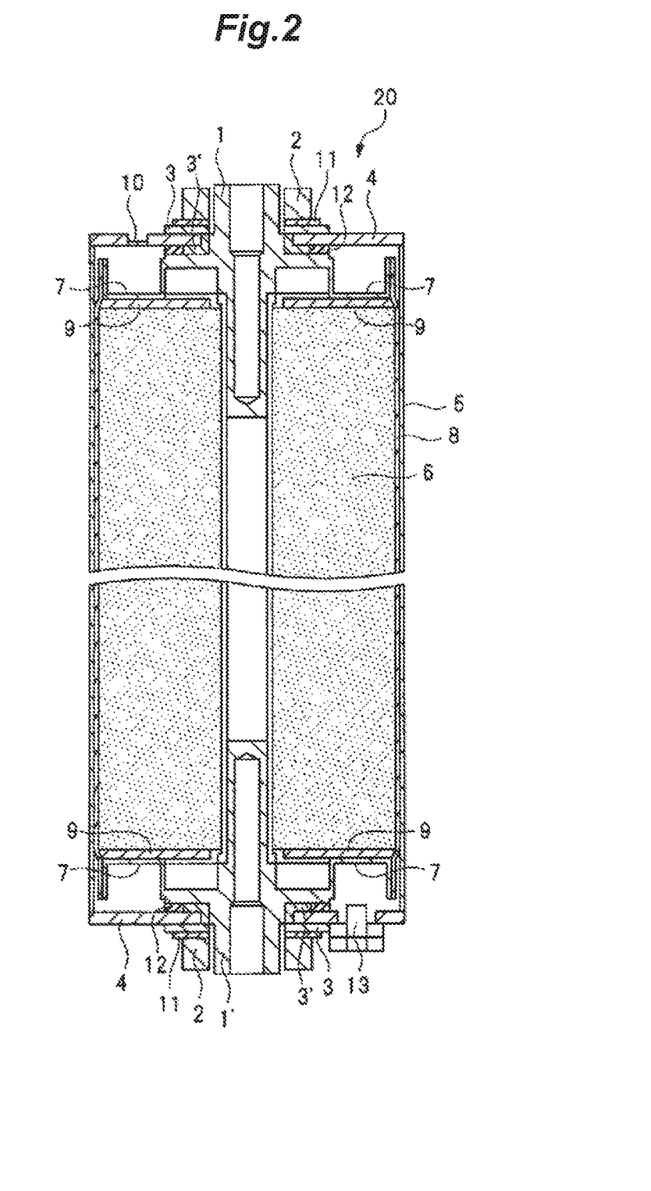
FIG. 2 is a sectional view of a columnar lithium-ion battery according to an embodiment of the present invention.

FIG. 2 is a sectional view of the lithium-ion battery. The positive electrode and the negative electrode were formed into a stacked member with a separator, which was made of polyethylene with a thickness of 30 μm, interposed therebetween such that the positive electrode and the negative electrode did not directly contact each other. The stacked member was wound to form an electrode group (electrode group of a wound type). In this event, the lead piece of the positive electrode and the lead piece of the negative electrode were located on end surfaces of the electrode group that are opposite to each other. The length of the positive electrode, the negative electrode, and the separator was adjusted such that the diameter of the electrode group was 65±0.1 mm.

Then, as illustrated in FIG. 2, lead pieces 9 led out from the positive electrode were deformed such that all of the lead pieces 9 were gathered in the vicinity of the bottom portion of a flange portion 7 on the positive electrode side to contact the flange portion 7. The flange portion 7 on the positive electrode side was integrally shaped to extend outward from the periphery of an electrode column (positive external terminal 1) located substantially on the extension of the axial core of an electrode group 6, and had a bottom portion and a side portion. After that, the lead pieces 9 were connected to the bottom portion of the flange portion 7 and fixed using ultrasonic welding. Lead pieces 9' led out from the negative electrode were also similarly connected to the bottom portion of the flange portion 7 on the negative electrode side and fixed. The flange portion 7 on the negative electrode side was integrally shaped to extend outward from the periphery of an electrode column (negative external terminal 1') located substantially on the extension of the axial core of the electrode group 6, and had a bottom portion and a side portion.

After that, the side portion of the flange portion 7 on the external positive terminal 1 side and the side portion of the flange portion 7 on the external negative terminal 1' side were covered using an adhesive tape to form an insulating covering 8. Similarly, an insulating covering 8 was also formed on the outer periphery of the electrode group 6. For example, the insulating covering 8 was formed by winding the adhesive tape over and over around the side portion of the flange portion 7 on the external positive terminal 1 side, then the outer peripheral surface of the electrode group 6, and then the side portion of the flange portion 7 on the external negative terminal 1' side. An adhesive tape, in which the base material was polyimide and to one surface of which an adhesive material made of hexamethacrylate was applied, was used as the insulating covering (adhesive tape) 8. The thickness of the insulating covering 8 (number of windings of the adhesive tape) was adjusted such that the largest diameter portion of the electrode group 6 was slightly smaller than the inside diameter of the battery container 5 made of stainless steel. The electrode group 6 was inserted into a battery container 5. The battery container 5 had an outside diameter of 67 mm and an inside diameter of 66 mm.

Then, as illustrated in FIG. 2, a ceramic washer 3' was fitted onto each of the electrode columns, the respective distal ends of which form the external positive terminal 1 and the external positive terminal 1'. The ceramic washer 3' was made of alumina. A portion of the ceramic washer 3' that abutted against the back surface of the battery lid 4 had a thickness of 2 mm, an inside diameter 16 mm, and an outside diameter of 25 mm. Then, the external positive terminal 1 was passed into the ceramic washer 3 with the ceramic washer 3 placed on the battery lid 4, and the external negative terminal 1' was passed into the different ceramic washer 3 with the different ceramic washer 3 placed on another battery lid 4'. The ceramic washer 3 was made of alumina, and had a flat plate shape with a thickness of 2 mm, an inside diameter 16 mm, and an outside diameter of 28 mm.

After that, the peripheral end surface of the battery lid 4 was fitted with an opening portion of the battery container 5, and the entire contact portions of the battery lid 4 and the battery container 5 were laser-welded to each other. In this event, the external positive terminal 1 and the external negative terminal 1' penetrated holes provided in the respective centers of the battery lids 4 and 4' to project to the outside of the battery lids 4 and 4'. The battery lid 4 was provided with a cleavage valve 10 configured to open according to a rise in internal pressure of the battery. The opening pressure of the cleavage valve 10 was 13 to 18 kg/cm$^2$.

Then, as illustrated in FIG. 2, a metal washer 11 was fitted onto each of the external positive terminal 1 and the external negative terminal 1'. Consequently, the metal washer 11 was disposed on the ceramic washer 3. The metal washer 11 was made of a material that was smoother than the bottom surface of a nut 2.

Then, the nut 2 made of metal was screwed to each of the external positive terminal 1 and the external negative terminal 1', and tightened to fix the battery lid 4, 4' between the flange portion 7 and the nut 2 via the ceramic washer 3, the metal washer 11, and the ceramic washer 3'. In this event, the tightening torque value was 70 kgf·cm. The metal washer 11 was not rotated until the tightening was finished. In this state, power generation elements inside the battery container 5 were blocked from outside air by compression of an O-ring 12 made of rubber (EPDM) which was interposed between the back surfaces of the battery lid 4, 4' and the flange portion 7.

After that, an electrolyte was poured into the battery container 5 from a liquid inlet port 13 provided in the battery lid 4'. The electrolyte was poured in a dry room. First, the maximum allowable amount of the electrolyte was measured. The electrolyte was poured in three times (three days). The electrolyte was separately poured in three days because it took time for the electrodes to be impregnated with the electrolyte. The electrolyte was poured using a desiccator in the first and second times. The pressure in the desiccator was reduced to −0.08 MPa (for some desiccators, the pressure value was indicated in a positive value, i.e., 0.08 MPa). The electrolyte was poured in such a reduced-pressure environment because the electrodes were easily impregnated with the electrolyte by removing air contained in the electrodes. After that, the electrolyte was poured by suctioning the electrolyte set outside the desiccator from a tube attached to one of release valves of the desiccator. This operation was performed twice (two days). The third pouring (on the third day) was performed without using the desiccator. This is because it was considered that almost all the air contained in the electrodes had already been removed in the first and second injections. If the pressure were reduced using the desiccator, the liquid surface of the electrolyte would be raised, which would reduce the amount of the electrolyte to be poured in the third injection. Thus, the desiccator was not used in the third time, and the electrolyte was directly poured from cups containing small portions of the electrolyte until immediately before the electrolyte overflowed from the liquid inlet port 13. The volume of the electrolyte at this time was determined as the maximum allowable amount, and the volume was also defined as the volume X of a void space in the battery container 5. With the amount of (volume occupied by) the poured electrolyte defined as Y, batteries were fabricated with the ratio (the value of Y/X) of the amount of (volume occupied by) the poured electrolyte to the volume of a void space in the battery container 5 being varied by changing the amount Y of (volume occupied by) the electrolyte injected. After the electrolyte was poured, the liquid inlet port 13 was sealed to fabricate a cylindrical lithium-ion battery 20.

As a result of measurement, the maximum allowable volume of the electrolyte, in other words, the volume of a void space in the battery container 5 was 350 cc. Lithium-ion batteries 20 with the value of Y/X being 0.60 to 1.00 were fabricated by varying the amount of the poured electrolyte from 205 to 350 cc.

A solution prepared by dissolving 1.2 mol/L of lithium phosphate hexafluoride ($LiPF_6$) in a mixed solution in which ethylene carbonate, dimethyl carbonate, and ethylmethyl carbonate were mixed with volume ratios of 2:3:2 was used as the electrolyte.

After the cylindrical lithium-ion battery 20 was fabricated, the cylindrical lithium-ion battery 20 was subjected to charge/discharge cycles for initialization and an aging process described below to complete the manufacturing process.

[Charge/Discharge Cycles for Initialization]

The cylindrical lithium-ion battery 20 was subjected to the charge/discharge cycles for initialization in an environment at a temperature of 25° C. The current value was 20 A for both charge and discharge. For the charge process, constant-current constant-voltage (CCCV) charge was performed with an upper limit voltage of 4.1 V, and ended in three hours. For the discharge process, constant-current (CC) discharge was performed, and ended at 2.7 V. A rest of 30 minutes was provided between the charge and the discharge. Three cycles of charge and discharge were performed.

[Aging]

After the charge/discharge cycles for initialization, the battery voltage was adjusted to 3.9 V, and left to stand for 21 days in an environment at 25° C.

[Check of Initial Capacity]

After the aging, constant current (CC) discharge was performed at 20 A to 2.7 V. After that, constant-current constant-voltage (CCCV) charge was performed at 20 A and with an upper limit voltage of 4.1 V for three hours. Further following that, constant current (CC) discharge was performed at 8 A to 2.7 V. A rest of 30 minutes was provided between the charge and discharge processes. The capacity after the discharge at 8 A was determined as the initial capacity of the battery. The average value of the initial capacities of the batteries used in this test was 47.5 Ah.

[Overcharge Test]

An overcharge test was performed using the battery of which the initial capacity had been checked (the battery which had been subjected to the discharge at 8 A to 2.7 V). The normal operation range of the battery used in this test was determined as 2.7 to 4.1 V, and charging the battery to a voltage above the range was defined as overcharge. The battery was subjected to constant-current (CC) charge at 60 A to 5.1 V, and the charge process was stopped when 5.1 V (124% of the upper-limit use voltage) was reached, and then the test was ended. A thermocouple had been affixed to the surface of the test battery to measure the temperature of the battery during the overcharge test. The state of the battery during the test was also observed. It was checked whether or not the battery was ruptured or ignited and whether or not the electrolyte was leaked from the battery.

(Example 1) to (Example 3)

Table 1 indicates the test results for batteries with the ratio (the value of Y/X) of the amount Y of (volume occupied by) a poured electrolyte to the volume X of a void space in the battery container 5 being 0.65 to 0.94.

TABLE 1

|  | Y/X | Whether battery was ruptured or ignited | Whether electrolyte was leaked | Battery surface temperature (° C.) when 5.1 V was reached |
| --- | --- | --- | --- | --- |
| Ex. 1 | 0.65 | No | No | 85 |
| Ex. 2 | 0.82 | No | No | 79 |
| Ex. 3 | 0.94 | No | No | 73 |

From Table 1, it was found that the batteries with the ratio (the value of Y/X) of the amount Y of (volume occupied by)

a poured electrolyte to the volume X of a void space in the battery container 5 being 0.65 to 0.94 were "not ruptured or ignited" and the "electrolyte was not leaked" from such batteries in the overcharge test.

The surface temperature of the battery at the time when 5.1V was reached was 85° C. or less for all the batteries according to Examples 1 to 3. This means that heat accumulated inside the lithium-ion battery was efficiently released to the outside of the battery when the value of Y/X was 0.65 or more. That is, this indicates that a current can be blocked when a set voltage for detecting voltage abnormality was reached before the temperature is significantly raised (thermal runaway of the battery can be suppressed, thereby increasing the safety of the battery).

In Example 2, the surface temperature of the battery was 79° C., which was lower than 85° C. in Example 1. This means that heat accumulated inside the lithium-ion battery was more efficiently released to the outside of the battery as a result of adjusting the value of Y/X to 0.82 which was larger than 0.65. That is, it indicates that a current can be blocked when the above abnormality detecting voltage was reached in a situation in which the temperature rise is gentle (thermal runaway of the battery can securely be suppressed, thereby furthermore increasing the safety of the battery).

In Example 3, further, the surface temperature of the battery was 73° C., which was lower than 79° C. in Example 2. This means that heat accumulated inside the lithium-ion battery was further more efficiently released to the outside of the battery when the value of Y/X was increased to 0.94 which was further larger than 0.82. In other words, it indicates that a current can be blocked when the above abnormality detecting voltage was reached in a situation in which the temperature has hardly been raised (as a result, thermal runaway of the battery can securely be suppressed, thereby furthermore increasing the safety of the battery 9.

(Comparative Example 1) and (Comparative Example 2)

Table 2 indicates the test results for batteries with the ratio (the value of Y/X) of the amount Y of (volume occupied by) a poured electrolyte to the volume X of a void space in the battery container 5 being 0.60 and 1.00.

TABLE 2

| | Y/X | Whether battery was ruptured or ignited | Whether electrolyte was leaked | Battery surface temperature (° C.) when "battery was ruptured or ignited" or "electrolyte was leaked" |
|---|---|---|---|---|
| Comp. Ex. 1 | 0.60 | Yes | Yes | 95 |
| Comp. Ex. 2 | 1.00 | No | Yes | 70 |

From Table 2, it was found that the battery with the ratio (the value of Y/X) of the amount Y of (volume occupied by) a poured electrolyte to the volume X of a void space in the battery container 5 being 0.60 was "ruptured or ignited" and the "electrolyte was leaked" from such a battery. It was also found that the battery with the ratio (the value of Y/X) of the amount Y of (volume occupied by) a poured electrolyte to the volume X of a void space in the battery container 5 being 1.00 was not "ruptured or ignited" but the "electrolyte was leaked" from such a battery.

In Comparative Example 1, the surface temperature of the battery at the time when 5.1 V was reached was 95° C., which was higher than those in Examples 1 to 3 (in the temperature range of 73° C. to 85° C.). This means that heat accumulated inside the lithium-ion battery was not easily released to the outside of the battery when the value of Y/X was less than 0.65. That is, it indicates that the temperature, at which a set voltage for detecting voltage abnormality is reached to block a current, is raised, thereby readily causing thermal runaway of the lithium-ion battery.

The reason that the battery was "not ruptured or ignited" and the "electrolyte was not leaked" in Example 1 and that the battery was "ruptured or ignited" and the "electrolyte was leaked" in Comparative Example 1 is presumed to be as follows. Table 3 indicates, as reference data, the battery surface temperature at the time when 5.1 V was reached or immediately before the occurrence of a phenomenon (herein, the battery was "ruptured or ignited" or the "electrolyte was leaked").

TABLE 3

| Y/X | Battery surface temperature (° C.) when 5.1 V was reached | Battery surface temperature (° C.) when "battery was ruptured or ignited" or "electrolyte was leaked." |
|---|---|---|
| 0.60 | — | 95 |
| 0.65 | 85 | — |
| 0.82 | 79 | — |
| 0.94 | 73 | — |
| 1.00 | — | 70 |

From Table 3, it can be known that the battery surface temperature at the time when 5.1 V was reached, or the battery surface temperature immediately before the occurrence of a phenomenon, was lower for a battery with a higher ratio (the value of Y/X) of the amount Y of (volume occupied by) a poured electrolyte to the volume X of a void space in the battery container 5, in other words, a battery with a larger amount of the electrolyte. This is considered to be because as the amount of the electrolyte is larger, heat generated in the electrode group during the overcharge is more easily conducted to the battery case and the battery has better heat radiation characteristics. As the battery temperature is lower, the internal resistance of the battery is larger, which raises the overvoltage and tends to raise the voltage during the overcharge, and the voltage for detecting a voltage abnormality is reached when the temperature rise is small (in particular, in a situation in which the temperature has hardly been raised or in a situation in which the temperature rise is gentle).

Figure 1:
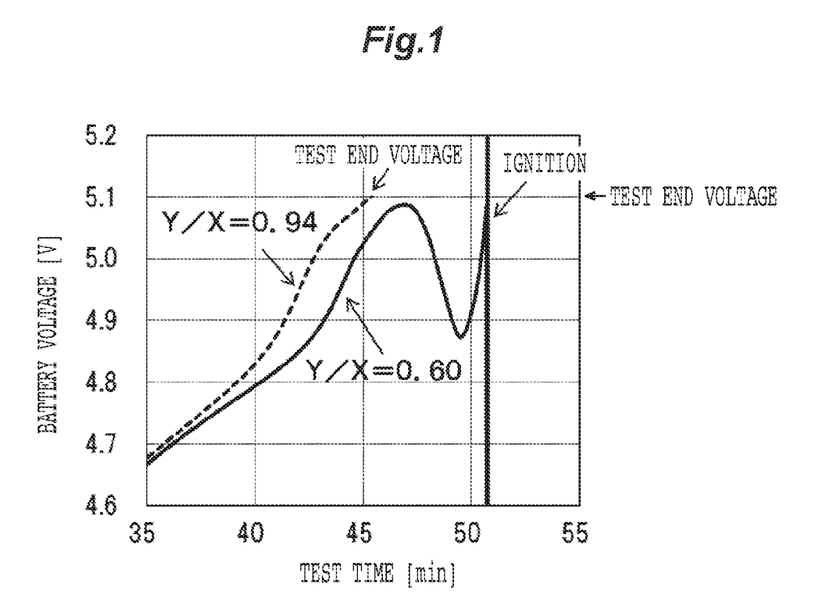
FIG. 1 illustrates transitions in voltage during an overcharge test of a battery when the ratio (the value of Y/X) of the amount Y of (the volume occupied by) an electrolyte poured into the battery container to the volume X of a void space in the battery container, in which the electrode group is placed, is set to 0.60 and 0.94.

FIG. 1 illustrates transitions in voltage, during the overcharge test, in respect of batteries with the ratio (the value of Y/X) of the amount Y of (volume occupied by) a poured electrolyte to the volume X of a void space in the battery container 5 being 0.60 and 0.94.

From FIG. 1, it can be known that the voltage was lowered once (about 47 minutes after the test started) before the voltage reached 5.1 V in respect to the battery of which the ratio (the value of Y/X) of the amount Y of (volume occupied by) a poured electrolyte to the volume X of a void space in the battery container 5 was 0.60. It is considered that there was a short-circuit inside the battery, and the voltage of the battery was abruptly raised and the temperature of the battery also abruptly rose, which led to ignition of the battery. Conversely, it is considered that the battery, of which the ratio (the value of Y/X) of the amount Y of (volume occupied by) a poured electrolyte to the volume X of a void space in the battery container 5 was 0.94, was not "ruptured or ignited" because the battery had better heat radiation characteristics than those of the battery with a ratio of 0.60 and consequently had a large internal resistance of the battery (i.e. a large voltage rise), and the test was finished when the set voltage (5.1 V) was reached in the early stage.

It follows from the foregoing that the heat radiation characteristics of the battery containing a large amount of the electrolyte were improved, and that the safety of the battery in case of overcharge was improved.

It is considered that the heat radiation characteristics of the battery, of which the ratio (the value of Y/X) of the amount Y of (volume occupied by) a poured electrolyte to the volume X of a void space in the battery container 5 was 1.00, was improved, but the electrolyte was leaked from the battery in the overcharge test. This is because the cleavage valve was opened when the battery was overcharged. It is presumed that, if the value of Y/X was 1.00, a large amount of gas was generated during the overcharge process, which increased the internal pressure of the battery and opened the cleavage valve to leak the electrolyte.

From the above results, it is possible to provide a lithium-ion battery that attains high safety when overcharged by forming a lithium-ion battery of a positive electrode, a negative electrode, a separator, and a non-aqueous electrolyte, wherein the positive electrode contains a layered composite oxide of lithium, nickel, manganese, and cobalt (NMC) as a main positive active material, the negative electrode contains amorphous carbon as a main negative active material, the separator is disposed between the positive electrode and the negative electrode, and the battery has a discharge capacity of 20 Ah or more with the ratio (the value of Y/X) of the amount Y of (volume occupied by) the poured electrolyte to the volume X of a void space in the battery container being 0.65 or more.

In the examples, the present invention is applied to a lithium-ion battery having an electrode group of a wound type (wound electrode group) as the electrode group. However, the present invention is not limited to such examples, and may be modified based on the technical concept of the present invention. That is, the lithium-ion battery according to the present invention may employ a stacked electrode group which is not wound, an electrode group that is wound into a flat shape, or the like. It should be noted, however, that the present invention is particularly suitable for use in a lithium-ion battery that has an electrode group of a wound type (wound electrode group).

DESCRIPTION OF REFERENCE NUMERALS

1 external positive terminal
1' external negative terminal
2 nut
3, 3' ceramic washer
4, 4' battery lid
5 battery container
6 electrode group
7 flange portion
8 insulating coating
9, 9' lead piece
10 cleavage valve
11 metal washer
12 O-ring
13 liquid inlet port
20 cylindrical lithium-ion battery

The invention claimed is:

1. A lithium-ion battery comprising an electrode group, an electrolyte, and a battery container that contains the electrode group and the electrolyte, the electrode group being formed by stacking a positive electrode and a negative electrode via a separator, the positive electrode containing a composite oxide of lithium, nickel, manganese, and cobalt as a main positive active material, the negative electrode containing amorphous carbon as a main negative active material, and the lithium-ion battery having a discharge capacity of 20 Ah or more, wherein a ratio (a value of Y/X) of a volume Y occupied by the electrolyte to a volume X of a void space in the battery container, with the electrode group being placed in the battery container, is 0.65 or more and 0.94 or less.

2. The lithium-ion battery according to claim 1, wherein the composite oxide of lithium, nickel, manganese, and cobalt is a layered composite oxide of lithium, nickel, manganese, and cobalt.

3. The lithium-ion battery according to claim 1, wherein the amorphous carbon is easily graphitizable carbon.

4. The lithium-ion battery according to claim 1, wherein the electrolyte is prepared by dissolving lithium hexafluorophosphate in a mixed solution prepared by mixing ethylene carbonate, dimethyl carbonate, and ethylmethyl carbonate.

5. The lithium-ion battery according to claim 1, wherein the discharge capacity is 20 Ah or more and less than 99 Ah.

6. The lithium-ion battery according to claim 1, wherein the electrode group is a wound electrode group.

7. The lithium-ion battery according to claim 2, wherein the amorphous carbon is easily graphitizable carbon.

8. The lithium-ion battery according to claim 2, wherein the electrolyte is prepared by dissolving lithium hexafluorophosphate in a mixed solution prepared by mixing ethylene carbonate, dimethyl carbonate, and ethylmethyl carbonate.

9. The lithium-ion battery according to claim 3, wherein the electrolyte is prepared by dissolving lithium hexafluorophosphate in a mixed solution prepared by mixing ethylene carbonate, dimethyl carbonate, and ethylmethyl carbonate.

10. The lithium-ion battery according to claim 2, wherein the discharge capacity is 20 Ah or more and less than 99 Ah.

11. The lithium-ion battery according to claim 3, wherein the discharge capacity is 20 Ah or more and less than 99 Ah.

12. The lithium-ion battery according to claim 4, wherein the discharge capacity is 20 Ah or more and less than 99 Ah.

13. The lithium-ion battery according to claim 2, wherein the electrode group is a wound electrode group.

14. The lithium-ion battery according to claim 3, wherein the electrode group is a wound electrode group.

15. The lithium-ion battery according to claim 4, wherein the electrode group is a wound electrode group.

16. The lithium-ion battery according to claim 5, wherein the electrode group is a wound electrode group.

* * * * *